United States Patent [19]

Cooper et al.

[11] 4,347,191

[45] Aug. 31, 1982

[54] PROCESS FOR THE PREPARATION OF 5-DIMETHYLAMINOMETHYL-2-FURAN-METHANOL

[75] Inventors: John Cooper, Tonbridge Wells; Dennis V. Lee, Leeds, both of England

[73] Assignee: Smith Kline & French Laboratories Limited, Welwyn Garden City, England

[21] Appl. No.: 240,651

[22] Filed: Mar. 5, 1981

[30] Foreign Application Priority Data

Mar. 8, 1980 [GB] United Kingdom ............... 8007943

[51] Int. Cl.$^3$ ........................................... C07D 307/52
[52] U.S. Cl. ..................................................... 549/492
[58] Field of Search ........................................ 260/347.7

[56] References Cited

U.S. PATENT DOCUMENTS

| | | | |
|---|---|---|---|
| 4,128,658 | 12/1978 | Price et al. ........................... | 424/285 |
| 4,233,302 | 11/1980 | Martin-Smith et al. ............ | 424/251 |
| 4,234,588 | 11/1980 | Brown et al. ........................ | 424/251 |
| 4,264,614 | 4/1981 | Clitherow et al. ................... | 424/267 |

OTHER PUBLICATIONS

Smith, Open—Chain Nitrogen Compounds, vol. 1, W. A. Benjamin, Inc., New York (1965) pp. 322–323.
Derwent Abstract 79110B (Belgian Patent 875,846).
Derwent Abstract 85985B (Belgian Patent 877,889).
Derwent Abstract 53014B (European 2930).
Derwent Abstract 61844B (European 3677).
Holdren, J. Amer. Chem. Soc. 69:464 (1947).
Gill et al., J. Chem. Soc. :4728 (1958).
Organic Syntheses, Coll. vol. 5:434–436.
deSolms, J. Org. Chem. 41:2650–2651 (1976).
Taylor et al., J. Org. Chem. 33:1719–1727 (1968).
Goldfarb et al., Chemical Abstracts vol. 69:59004g (1968).
Holdren, J. Am. Chem. Soc. 69:464 (1947).

Primary Examiner—Richard Raymond
Attorney, Agent, or Firm—Joan S. Keps; Richard D. Foggio; Alan D. Lourie

[57] ABSTRACT

A process for preparing 5-dimethylaminomethyl-2-furanmethanol by reacting 2-furanmethanol with bis(-dimethylamino)methane. The product is useful as a chemical intermediate, in particular to prepare $H_2$-histamine antagonists.

5 Claims, No Drawings

PROCESS FOR THE PREPARATION OF 5-DIMETHYLAMINOMETHYL-2-FURANMETHANOL

This invention relates to an improved process for making 5-dimethylaminomethyl-2-furanmethanol, which is a useful chemical intermediate.

In particular 5-dimethylaminomethyl-2-furanmethanol is useful in preparing $H_2$-histamine antagonists incorporating the 5-dimethylaminomethyl-2-furanmethylthio group, and these may be made directly by reaction with the appropriate thiol under acidic conditions or indirectly by initial conversion of the methanol into for example the methyl acetate or a methyl halide and subsequent reaction with a thiol, and if necessary further reactions to elaborate thiol-substituents. Specific $H_2$-histamine antagonists incorporating the 5-dimethylaminomethyl-2-furanmethylthio group are described in Belgian Pat. Nos. 875846 and 877889, U.S. Pat. No. 4,128,658 and European patent specifications Nos. 2930 and 3677, and three such compounds are:

N-[2-(5-dimethylaminomethyl-2-furanylmethylthio)ethyl]-N'-methyl-2-nitro-1,1-ethenediamine,
2-[2-(5-dimethylaminomethyl-2-furanylmethylthio)ethylamino]-5-(3-pyridylmethyl)-4-pyrimidone and
2-[2-(5-dimethylaminomethyl-2-furanylmethylthio)ethylamino]-5-(6-methyl-3-pyridylmethyl)-4-pyrimidone Published procedures for making 5-dimethylaminomethyl-2-furanmethanol involve reacting 2-furanmethanol (furfuryl alcohol) with dimethylamine hydrochloride and formaldehyde or paraformaldehyde, or involve the reduction of 5-dimethylaminomethyl-2-furancarboxylic acid methyl ester with lithium aluminium hydride. The latter route uses lithium aluminium hydride which is expensive and can be hazardous and uses a starting furan derivative which is expensive and is not freely available. We have found that the former route gives a product which is difficult to purify by distillation and which often after distillation contains impurities. The impurities tend to give problems of purification after the product is reacted with cysteamine in acetic acid or another acid medium. These difficulties are much more serious with large-scale preparations.

In a series of experiments with 2-furanmethanol we have found that the use of bis(dimethylamino)methane gives better yields of 5-(dimethylaminomethyl)-2-furanmethanol than those obtained using dimethylamine and a source of formaldehyde (e.g. aqueous formaldehyde, paraformaldehyde and trioxan). Furthermore the product obtained after distillation was also purer. The yields referred to above were 76–94% and these compare very favourably with the yields reported by R. F. Holdren (12%) (J. Amer. Chem. Soc. 69(464)1947) and Gill and Ing (70%) (J. Chem. Soc. 4728 (1958)).

According to the invention we provide a process for preparing 5-(dimethylaminomethyl)-2-furanmethanol (3)

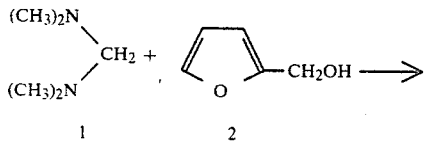

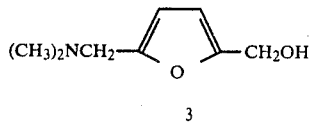

which comprises reacting 2-furanmethanol (2) with bis(dimethylamino)methane (1).

Preferably the reaction is carried out under acidic conditions, for example in acetic acid, or in a aprotic solvent, for example dichloromethane, containing an acid, for example acetic acid or hydrogen chloride. The reaction can also be carried out in the absence of an acid, for example in toluene, dichloromethane or 1,2-dichloroethane.

The reaction is exothermic and preferably the reaction is carried out at 0° C. to room temperature e.g. 0°–20° C. with external cooling during the addition of reagents.

The product can be isolated by concentration of the reaction mixture, basification, partition between water and an immiscible solvent, for example ethyl acetate, and concentration and distillation of the material extracted into the solvent.

An additional advantage offered by the invention is that the process can be carried out in the absence of halide ions and formaldehyde which could give rise to halomethyl ether impurities in the product.

A further advantage of the invention is that it can be carried out at or below room temperature, rather than requiring prolonged heating under reflux.

An aqueous solution of bis(dimethylamino)methane can be conveniently prepared by reacting aqueous formaldehyde with 2 molar equivalents of dimethylamine at 0°–15°. The anhydrous material can be obtained by drying with potassium hydroxide pellets and distillation.

5-Dimethylaminomethyl-2-furanmethanol can be converted into 2-(5-dimethylaminomethyl-2-furanylmethylthio)ethylamine by heating under reflux in acetic acid with cysteamine and can be further converted into various histamine $H_2$-antagonists for example, by reacting with a substituted pyrimidone to give 2-2-(5-dimethylaminomethyl-2-furanylmethylthio)ethylamino-5-(6-methyl-3-pyridylmethyl-4-pyrimidone by methods described in EP 3677.

The invention is illustrated by the following Examples:

EXAMPLES

Example 1

A solution of bis(dimethylamino)methane (112 g, 1.1 mol) in acetic acid (200 ml) was added dropwise with cooling (10° C.) to a stirred solution of 2-furanmethanol (98 g, 1.0 mol) in acetic acid (1000 ml). The mixture was stirred at room temperature for 18 hours and acetic acid was removed at 60° C. under reduced pressure. Ice (200 g) was added to the residue which was made basic with 40% aqueous sodium hydroxide (with external cooling). The mixture was extracted with ethyl acetate and the extracts were evaporated and distilled to give 5-dimethylaminomethyl-2-furanmethanol (145 g, 94%) b.p. 92°–96° C./0.2 0.5 mmHg.

Example 2

Hydrogen chloride is bubbled through a pre-cooled (10° C.) solution of bis(dimethylamino)methane and 2-furanmethanol in dichloromethane with stirring. As the reaction progresses the temperature of the reaction mixture rises and is allowed to continue to rise to room temperature. When the reaction is complete water is added. The dichloromethane layer is extracted with water and discarded. The aqueous layer is made basic with 40% aqueous sodium hydroxide (with external cooling) and extracted with ethyl acetate. The ethyl acetate extracts are dried and evaporated. The residue is distilled to give 5-dimethylaminomethyl-2-furanmethanol b.p. 92°–96° C./0.2 0.5 mmHg.

What is claimed is:

1. A process for preparing 5-dimethylaminomethyl-2-furanmethanol which comprises subjecting 2-furanmethanol to a Mannich reaction accomplished using bis(dimethylamino)methane.

2. A process according to claim 1 in which the reaction is carried out under acidic conditions.

3. A process according to claim 1 or claim 2 in which the reaction is carried out in the absence of halide ions and formaldehyde.

4. A process according to claim 2 in which the reaction is carried out in acetic acid.

5. A process according to claim 2 in which the reaction is carried out in dichloromethane containing hydrogen chloride.